United States Patent [19]

Aday

[11] 4,406,363
[45] Sep. 27, 1983

[54] FOLDER RETAINER FOR MULTISTRAND SURGICAL SUTURES

[75] Inventor: Jorge L. Aday, New Brunswick, N.J.

[73] Assignee: Ethicon, Inc., Somerville, N.J.

[21] Appl. No.: 422,986

[22] Filed: Sep. 24, 1982

[51] Int. Cl.³ .............................................. A61L 15/00
[52] U.S. Cl. .................................. 206/63.3; 206/476; 206/484; 206/628
[58] Field of Search .................... 206/63.3, 476, 484, 206/628, 438, 477, 482, 483, 488, 489, 491, 492

[56] References Cited

U.S. PATENT DOCUMENTS

| | | | |
|---|---|---|---|
| 3,206,018 | 9/1965 | Lewis et al. | 206/63.3 |
| 4,063,638 | 12/1977 | Marwood | 206/63.3 |
| 4,120,395 | 10/1978 | Mandel | 206/63.3 |
| 4,126,221 | 11/1978 | Cerwin | 206/63.3 |
| 4,253,563 | 3/1981 | Komarnycky | 206/63.3 |

Primary Examiner—Joseph Man-Fu Moy
Attorney, Agent, or Firm—Robert L. Minier

[57] ABSTRACT

A folder retainer having plurality of surgical sutures, the retainer comprising three panels with surfaces of two of the panels covered with a foam member. A retainer includes a fourth panel which locks the retainer in its folded configuration.

12 Claims, 14 Drawing Figures

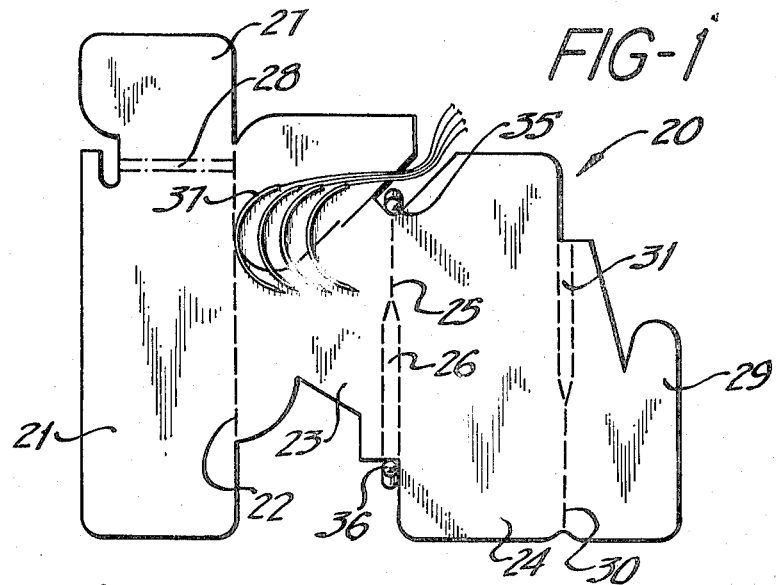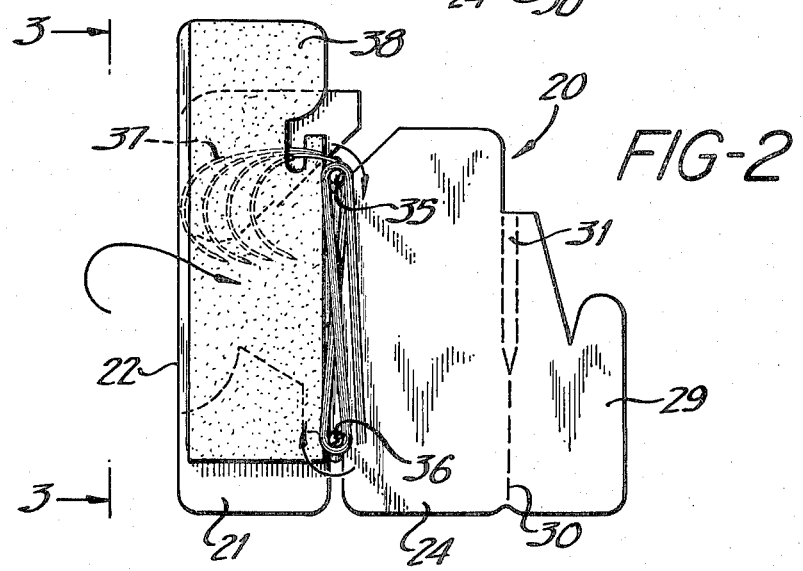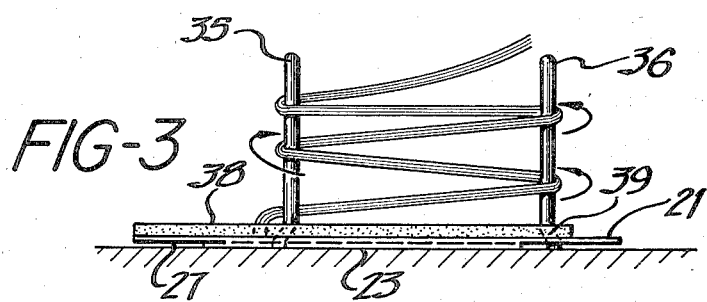

FOLDER RETAINER FOR MULTISTRAND SURGICAL SUTURES

BACKGROUND OF THE INVENTION

This invention relates to packages for surgical sutures and more particularly to a multi-panel, folded paper retainer for a plurality of coiled structures having needles attached hereto.

Packages for surgical sutures are constructed according to the nature of the suture and its intended use. In general, the ideal package holds and protects the suture during handling and storage, but allows the suture to be readily removed with a minimum of handling and difficulty.

One specific package consists of a folded paper suture retainer contained in a sterile, hermetically sealed envelope. The sterility of the suture in the envelope is maintained by a second sealed overwrap. When the suture is about to be used, the outerwrap is opened in the operating room, and the sealed envelope deposited in a sterile area. Sterile personnel thereupon tear open the envelope to gain access to the suture. A simplified improved suture package which allows simplified access to the package is described in U.S. Pat. No. 3,939,696. Also, in many surgical procedures, the surgeon employs a large number of sutures and, hence, very often packages will be provided that contain multistrands of sutures. The major problem with multiple suture packages has been to provide a means for allowing individual sutures to be removed from the package without entanglement. Recently, suture packages have been developed to retain a bundle of sutures in a predetermined coiled configuration which permits, for the most part, individual sutures to be withdrawn from the package without entangling the remaining sutures. Such multistrand packages with single strand access are illustrated in U.S. Pat. Nos. 4,089,409 and 4,126,221.

These multistrand packages have been improved by new packages of the multistrand type with the needled ends of the sutures being automatically presented when the sterile envelope is opened. Such packages are illustrated in U.S. Pat. No. 4,253,563.

The multistrand suture packages described in the abovereferenced patents provide a very acceptable package to the operating room personnel; however, the packages are difficult to produce. One problem is to wind the sutures appropriately and maintain them in the wound condition so they are not even slightly moved when the retainer is folded and, hence, are correctly removed when opened for use by the operating room personnel. One way of assisting in the manufacture or the winding of the suture and the placement of it in its retainer is more fully described in co-pending commonly assigned patent application Ser. No. 359,403 filed Mar. 18, 1982. In that application, a foam piece is used to act as a locking mechanism or holding mechanism for the coiled sutures.

The present invention represents a further improvement in packages of the multistrand type where the ends of the suture are automatically presented when the sterile envelope is opened. It is an object of the present invention to produce a retainer which is simple to use and assists in holding the sutures in place in their coiled configuration while the retainer is being folded and locked for further manipulation. It is a further object of the present invention to provide a folded suture retainer from which individual suture strands may be removed while insuring that only one strand is removed at a time and also that while removing that strand other strands within the package are not entangled or displaced.

SUMMARY OF THE PRESENT INVENTION

The present invention provides a folded retainer for a plurality of surgical sutures. The sutures are disposed in the retainer in a coiled or similar configuration so that they have a plurality of return bend sections. In the preferred embodiments of the present invention, the coils are narrow and long in shape and have return bend sections disposed at opposite ends of the coil. The retainer itself comprises a first and second suture retaining panel foldably connected along one major edge thereof. A third suture retaining panel is foldably connected to a minor edge of the first suture retaining panel. A foam member covers substantially the entire surface of one side of the first and third suture retaining panels. A fourth locking panel is foldably connected to the other major edge of the second suture retaining panel.

The desired coiled suture configuration is conveniently obtained by winding the suture bundle or plurality of sutures about two vertical pins. The pins are positioned at the ends of the foldably line between the first and second suture retaining panels. The winding starts at the bottom of the pins and the sutures are wound in an upward spiral to provide a plurality of convolutions disposed in sequence over the length of the suture and laterally displaced along the length of the pins. The sutures may be wound around the pins in a series of figure 8, or circular loops, as desired. The retainer is folded by placing the foam surface of the first suture retaining panel in contact with the sutures. This is accomplished by folding the first suture retaining panel vertically upwardly adjacent the pins so its foam surface contacts the sutures. The third suture retaining panel is folded about a pin so that its foam surface contacts the opposite surface of the sutures and covers the return bends of the sutures about one pin.

The second suture retaining panel is folded vertically upwardly on the opposite side of the coiled sutures and the pins removed, leaving the sutures lying in the position they were placed on the pins between the first and second suture retaining panels. The fourth locking panel is folded over the first suture retaining panel and locked therewith by any of the standard well known interlocking mechanisms that are used to lock suture panels together.

A preferred embodiment of the folded retainer of the present invention for use with a plurality of multistrand surgical sutures having needles attached with the sutures disposed in the retainer in a coiled or similar configuration and having a plurality of return bend sections with half of the bend sections disposed in opposed relationship to the other half of the bend sections comprises along with the first four panels and the foam member a needle retaining panel. The first and second suture retaining panels are foldably connected to the needle retaining panel with one suture retaining panel connected to one major edge and the other suture retaining panel connected to the other major edge of the needle retaining panel. The third suture retaining panel is foldably connected along at least a portion of a minor edge of the first suture retaining panel. Preferably, there is an opening disposed in the foldable edge between the first and third suture retaining panels to allow the suture threads to pass through the opening and connect with the needles attached to the sutures. A foam member covers substantially the entire surface of one side of the first and third suture retaining panels. The retainer includes a fourth locking panel foldably connected along the other major edge of the second suture retaining panel. The fourth locking panel is not as wide as the other panels of the retainer and has a finger portion along its longitudinal free edge adapted to cooperate or be inserted between the folded needle retaining panel and first suture retaining panel.

The unfolded retainer is placed about two vertical pins which extend at the ends of the fold line between the needle retaining panel and the second suture retaining panel. The retainer is placed with the foam member on the first and third suture retaining panels facing downwardly. Preferably, the pins have a step at their base so the sutures when wound on the pins are wound a spaced distance from the base of the pins. The reason for this spacing is so the foam member, when properly folded, contacts all the sutures. The sutures are wound in an upward spiral to provide a plurality of convolutions disposed in sequence over the length of the sutures and laterally displaced along the length of the pins. The sutures may be wound around the pins in a series of figure 8 or circular loops so that the return bends are produced in the sutures at the opposite ends of the coil. Prior to winding up the sutures, the needles are appropriately placed on the needle retaining panel. The first suture retaining panel is folded on top of the needles on the needle retaining panels. The suture threads are brought up through the opening in the foldable line between the third and first suture retaining panels. The sutures are wound on the pins as previously described. Upon being wound on the pins, the foam surface of the first surface retaining panel is folded against one side of the wound coiled sutures and the third suture retaining panel is folded about the pin to contact the opposite side of the coiled sutures so that the foam covers one-half of the return bends of the coiled sutures. The second suture retaining panel is folded on the side of the sutures on which the third suture retaining panel had been folded and the pins removed. The fourth locking panel is folded about the needle retaining panel and the finger is inserted in the space between the needle retaining panel and the first suture retaining panel to lock the retainers together and hold the sutures in place.

In the preferred embodiments of the folder of the present invention, there are gussets or double fold lines between the needle retaining panel and the second suture retaining panel, and also between the second suture retaining panel and the fourth locking panel. These gussets are preferred because of the depth to the foam member. The depth to the folds allows for folding of the panels without crushing the sutures in to the foam member. In a preferred embodiment of the present invention, the needle retaining panel includes a diagonal diecut area which allows for a portion of the panel to be readily displaced from the remainder of the panel and provide access to the needles. A needle may be easily grasped by a suitable needle holder and a needle and individual suture thread attached thereto readily and easily removed from the package without disturbing the remaining sutures.

The folded retainer and sutures contained therein may be sterilized and sealed in a conventional sterile envelope which preferably comprises aluminum foil coated with a thermo-plastic polymer and heat sealed about the periphery thereof. The portion of the needle retaining panel intended to be displaced or removed from the remainder of the panel to gain access to the suture needles is provided with a tab which extends beyond the width of the folded retainer. This tab is sealed in the border of the outer envelope so that when the envelope is opened by tearing one end, the portion of the needle retaining panel defined by the diagonal diecut line is simultaneously opened to expose the needled ends of the suture.

BRIEF DESCRIPTION OF THE DRAWINGS

The invention will be more fully described when taken in conjunction with the following drawings wherein:

FIG. 1 is a plan view of an unfolded suture retainer of the present invention as it is initially placed on pins and with needles positioned on the needle retaining panel;

FIG. 2 is a plan view of the suture retainer of FIG. 1 with the first suture retaining panel folded on top of the needle retaining panel and with the sutures wound on vertical pins;

FIG. 3 is a side view taken at line 3—3 of FIG. 2;

DETAILED DESCRIPTION OF THE DRAWINGS

Figure 4:
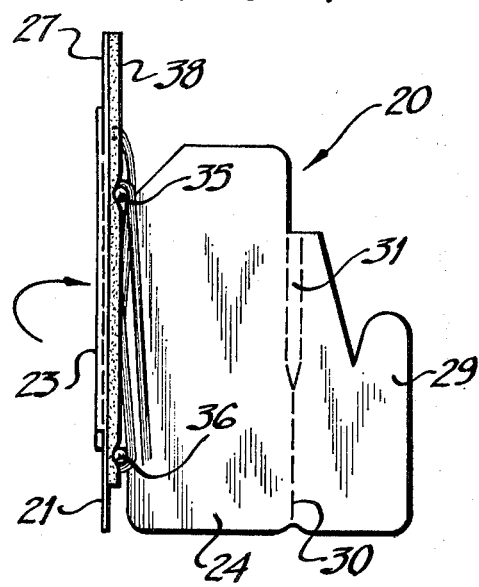
FIG. 4 is a plan view of the suture retainer of FIG. 2 with the first suture retaining panel and the needle retaining panel folded vertically adjacent the sutures wound on the pins.
Figure 5:
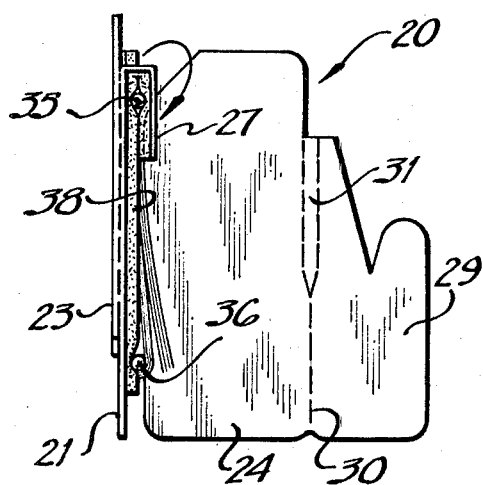
FIG. 5 is a plan view of the suture retainer of FIG. 4 with the third suture retaining panel folded about a pin to the first suture retaining panel.
Figure 6:
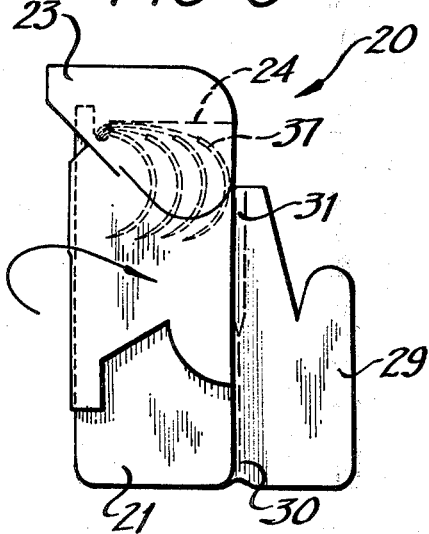
FIG. 6 is a plan view of the suture retainer of FIG. 5 with the second suture retaining panel folded in contact with the first suture retaining panel and with the retainer removed from the pins.
Figure 7:
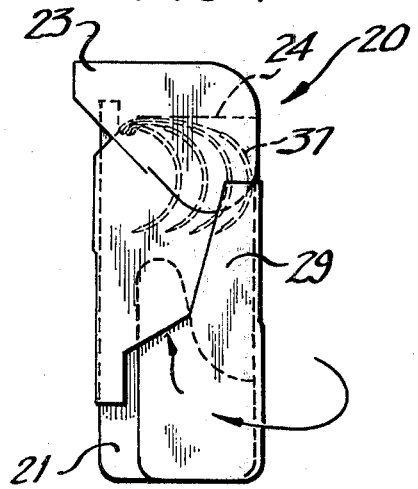
FIG. 7 is a plan view of the suture retainer of FIG. 6 with the fourth locking panel folded to lock the panels together.

Referring to the drawings in FIGS. 1 through 7, identical numerals are used for identical parts in each of these figures to aid in the description of the retainer. As seen in FIG. 1, the retainer 20 comprises a first suture retaining panel 21 foldably connected along one major edge 22 of a needle retaining panel 23. A second suture retaining panel 24 is foldably connected along the other major edge 25 of the needle retaining panel. The fold 25 has a gusset 26 or thickness along at least a portion of the fold to provide some depth to the final folded retainer. The retainer includes a third suture retaining panel 27 foldably connected along a minor edge 28 of the first suture retaining panel. A fourth locking panel 29 is foldably connected to the other major edge 30 of the second suture retaining panel. Again, this fold line between the locking panel and the second suture retaining panel preferably has a width or gusset 31 to provide depth to the folded retainer. In FIG. 1, the unfolded retainer is placed about pins 35 and 36 on which sutures may be wound. The retainer is placed over the pins so the needle retaining panel and the suture retaining panel straddle the pins as shown. Appropriate needles 37 of armed sutures are placed on the needle retaining panel. As seen in FIG. 2, the first suture retaining panel with its connected third suture retaining panel is folded over on to the needle retaining panel to encase the needles. The exposed or upper surface of the first and third suture retaining panel are substantially covered with a foam material 38. The sutures are wound up the pins as shown in FIG. 3. The sutures may be wound in a figure 8 or in a circular configuration as desired. The vertical pins as shown in FIG. 3 have a slight offset 39 or step at the bottom approximately in the same plane as the top of the foam. This provides that the sutures are started to be wound at the depth of the foam so that all of the sutures will, in fact, contact the foam in the final folded retainer. After the sutures have been wound up the pins, the needle retaining panel and the first suture retaining panel along with the attached third suture retaining panel are folded vertically upward so that the foam surface of the first suture retaining panel contacts and frictionally engages one side of the wound sutures as seen in FIG. 4. The third suture panel is folded about the return bends of the sutures on the upper pin to frictionally contact these return bends and lock the sutures in place as seen in FIG. 5. The second suture retaining panel is folded towards the pins, while the pins are being removed, and the second suture retaining panel encases the wound sutures while the frictional contact of the foam surfaces locks the sutures in their coiled configurations. The locking panel is folded over the needle retaining panel and the finger of the locking panel inserted beneath the needle retaining panel as seen in FIG. 7 to interlock all of the panels together. The final folded retainer encases the needles in a separate retaining compartment between the needle retaining panel and the first suture retaining panel and encases the suture threads between the first, second and third suture retaining panels with the foam surfaces of the first and third suture retaining panels frictionally contacting half of the return bends of the coiled sutures.

The foam, which makes excellent frictional contact with the sutures, insures that the sutures remain in their configuration throughout the further packaging, sterilization, transportation and manipulation of the suture package. Furthermore, the foam package insures that the coiled configurations of the sutures is maintained while the outerwraps are removed and maintains the sutures in their place as individual sutures are removed from the package. This positive holding of the sutures prevents either the removal of a plurality of sutures at one time or the entanglement of sutures within the package.

Figure 8:
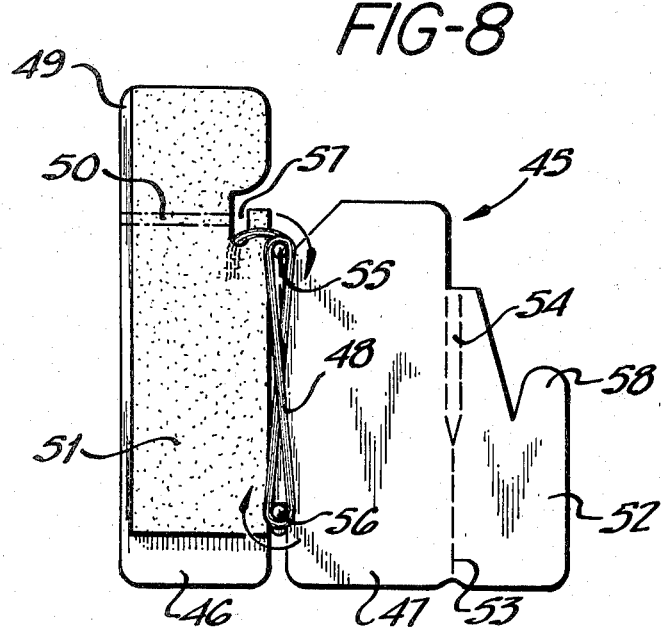
FIG. 8 is a plan view of another embodiment of an unfolded suture retainer of the present invention with the retainer disposed on vertical pins and with the suture being wound about those pins.
Figure 9:
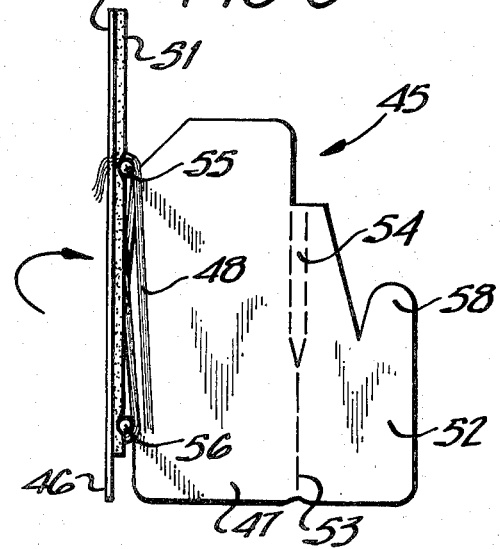
FIG. 9 is a plan view of the retainer of FIG. 8 with the first suture retaining panel folded vertically in contact with the sutures.
Figure 10:
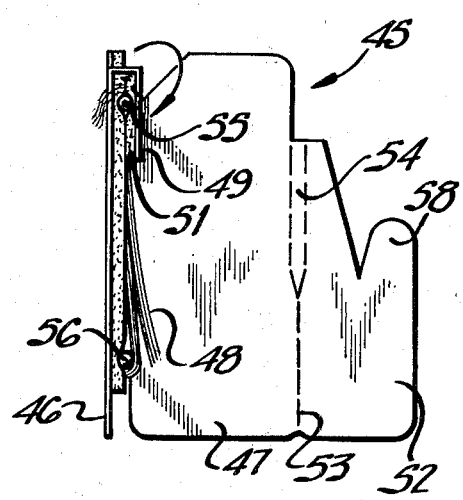
FIG. 10 is a plan view of the retainer of FIG. 9 with the third suture retaining panel folded about a pin onto the first suture retaining panel.
Figure 11:
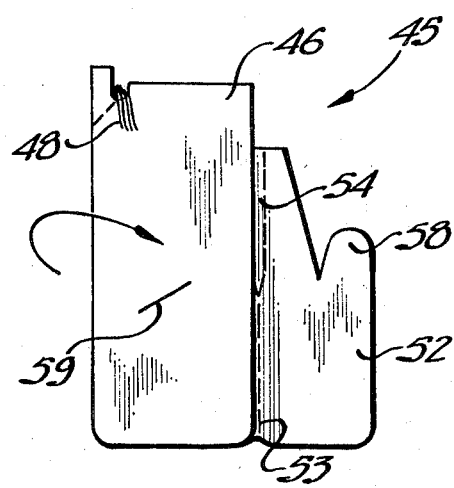
FIG. 11 is a plan view of the suture retainer of FIG. 10 with the second suture retaining panel folded to the first suture retaining panel.
Figure 12:
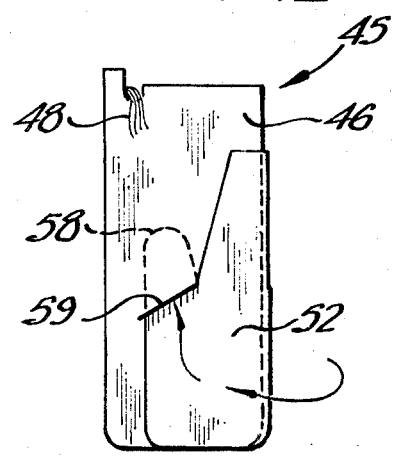
FIG. 12 is a plan view of the suture retainer of FIG. 11 with the fourth locking panel locked with the first suture panel.

In FIGS. 8 through 12 there is shown another embodiment of a suture retainer of the present invention. Identical numerals are used for identical parts in each of these figures to aid in the description of the retainer. In this embodiment, the retainer 45 comprises first and second suture retaining panels 46 and 47, respectively, foldably connected along one major edge 48 thereof. A third suture retaining panel 49 is connected to the first suture retaining panel along a minor edge 58 thereof. The first and third suture retaining panels have substantially the entire surface of one side of the panels covered with a foam material 51. A fourth locking panel 52 is connected to the other major edge 53 of the second suture retaining panel. The fold between these two panels preferably has some depth to it or a gusset 54. The unfolded retainer is placed over suitable vertical winding pins 55 and 56 with the first and second suture retaining panels straddling the pins as shown in FIG. 8. The ends of the sutures are placed in the opening 57 between the first and third suture retaining panels and are wound in the desired figure 8, serpentine or circular configuration, as desired, on the pins. When completely wound on the pins, the first suture retaining panel is folded upwardly as shown in FIG. 9 so the foam material contacts one side of the wound sutures. The third suture retaining panel is folded downwardly about the sutures so the foam surface contacts the return bend of the sutures about the upper pin as shown in FIG. 10. The second suture retaining panel is folded upwardly and the vertical pins removed from the retainer leaving the sutures locked in place by the foam between the first, second and third suture retaining panels and with the ends of the sutures protruding from the opening as shown in FIG. 11.

The fourth locking panel is folded over the first suture retaining panel and a portion 58 inserted in a slot 59 in the first suture retaining panel to lock the panels together and lock the sutures in place.

Figure 13:
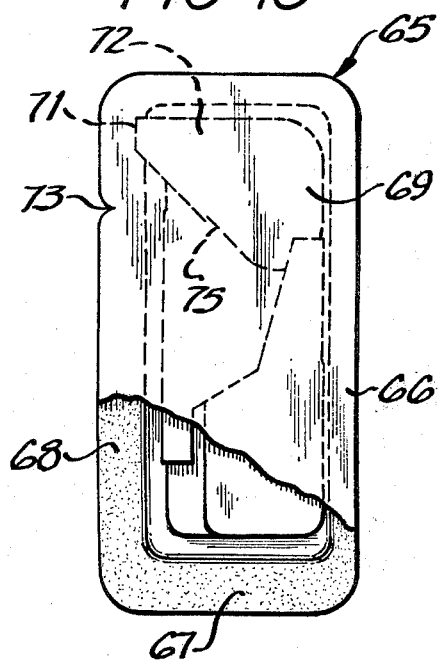
FIG. 13 is a plan view of the completely folded suture retainer of FIG. 1 contained within a sealed outer envelope.
Figure 14:
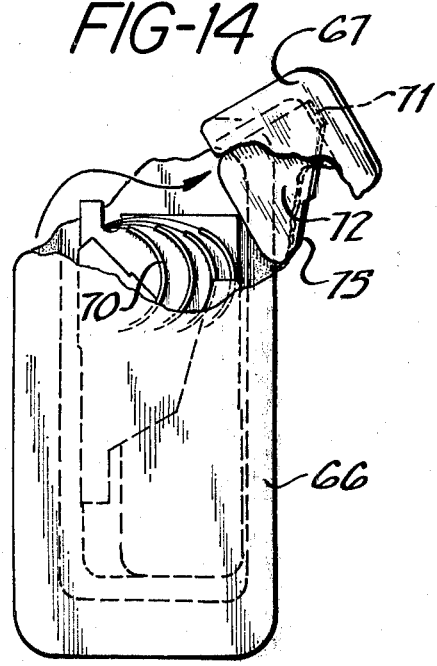
FIG. 14 is a plan view of the suture package and envelope of FIG. 13 opened to provide access to the sutures.

The suture retainers with the sutures and needles therein may be packaged and sterilized by various techniques as is well known in the art. In FIGS. 13 and 14, one specific package is shown. The package 65 depicted is a conventional suture package formed by heat sealing the periphery of two panels 66 and 67 of aluminum foil coated on the interior surfaces thereof with a heat sealable polymeric composition 60. Other means for sealing may be employed as desired. Disposed within the envelope is a prefolded retainer 69 such as that depicted in FIG. 7 with multiple sutures and needles 70 which have been sterilized and sealed within the envelope. A tab 7 of the needle retaining panel 7R projects slightly beyond the width of the retainer and is secured in the sealed periphery of the envelope. A tear notch 73 is provided in the outer edge of the envelope and located approximately at the lower edge of the tab to facilitate the opening of the suture package when tearing the outer envelope. The suture package as illustrated in FIG. 13 is hermetically sealed and may be stored for extended periods of time. When the sutures are to be removed from the package, the outer envelope is opened by tearing the notch as illustrated in FIG. 7. Since the tab is secured in the sealed periphery of the envelope, the needle retaining panel is simultaneously torn as the envelope is opened exposing the needles. The needle retaining panel is made to tear diagonally across the width of the retainer guided by the edge of diecut portion 75. This tearing exposes the needles, and it is a simple matter to grasp a needle with a suitable needle holder and remove an individual suture from the package without disturbing any of the other sutures.

The suture retainer of the present invention is preferably constructed of a heavyweight stiff paper or paperboard such as 5 to 12 solid bleached sulfate board. The paperboard is foldable and yet sufficiently strong and stiff to support the suture and provide relatively rigid packages. Similar materials, including plastic foils and laminates of these with each other or with paper, may also be used with good results. the suture retainer may be readily diecut from such materials by a single die which also forms the desired fold lines including the necessary gussets in accordance with the present invention.

The foam member may be made from any of the standard foam materials such as polyethers, polyesters, and the like. The foam sheets are usually less than one-eighth inch thick and cover substantially the entire surface of the appropriate suture retaining panels. The foams may be secured to the panels by any of the pressure sensitive adhesives well known in the art which may be applied to the surface of the foam and the foam secured to the panels.

Sutures packaged in three to eight strands or more may be individually removed from the packages of the present invention by simply grasping an exposed end of a single suture and withdrawing the suture with a steady pull.

Sutures packaged in accordance with the present invention may be multifilament or monofilament sutures and the multifilament sutures may be braided, twisted or covered. In addition, the sutures may be packaged with or without needles attached to the end of the suture.

The preceding description has been directed primarily to the preferred embodiments of the present invention, and many variations which nevertheless employ the essential features thereof will be apparent to those skilled in the art. For example, while the foregoing has described the folded to be employed with vertical winding pins, the suture may be coiled and positioned in the package with any convenient means that will permit single strand delivery from the folded package. Thus, the winding pins may be omitted from certain cases or other structures may be added if required by the intended folding method. These and other variations are accordingly included within the scope of the present invention.

I claim:

1. A folded retainer for a plurality of surgical sutures, said sutures being disposed in said retainer in a coiled or similar configuration having a plurality of return bend sections with one-half of said bend sections being disposed in opposed relationship to the other half of said bend sections, comprising:
   first and second suture retaining panels foldably connected along one major edge thereof,
   a third suture retaining panel foldably connected along one minor edge of said first suture retaining panel;
   a foam member covering substantially the entire surface of one side of said first and third suture retaining panels;
   a fourth locking panel foldably connected along the other major edge of the second suture retaining panel;
   said retainer, when folded with said third suture retaining panel with the form thereon folded on to the first suture retaining panel with the foam surfaces in face-to-face relationship, said foam member covers one-half of the return bends of said surgical sutures and with said fourth locking panel folded over said first suture retaining panel to lock therewith.

2. A folded retainer for a plurality of surgical sutures according to claim 1 wherein the foam member covering substantially the entire surface of one side of said first and third suture retaining panels is an integral member.

3. A folded retainer according to claims 1 or 2 wherein the fourth locking panel includes a finger adapted to be inserted into a slit in the back of the first suture retaining panel to interlock the panels together.

4. A folded retainer for a plurality of needled surgical sutures, said sutures being disposed in said retainer in a coiled or similar configuration having a plurality of return bend sections with one-half of said bend sections being disposed in opposed relationship to the other half of said bend sections, comprising:
   a needle retaining panel;
   first and second suture retaining panels foldably connected to said needle retaining panel with said first suture retaining panel connected along one major edge of said needle retaining panel and the second suture retaining panel connected along the other major edge of said needle retaining panel;
   a third suture retaining panel foldably connected along at least a portion of one minor edge of said first suture retaining panel;
   a foam member covering substantially the entire surface of one side of said first and third suture retaining panels;
   a fourth locking panel foldably connected along the other major edge of the second suture retaining panel;
   said retainer, when folded with said third suture retaining panel with the foam thereon folded on to the first suture retaining panel with the foam thereon with the foam surfaces in face-to-face relationship to cover half of the return bends of said surgical sutures with said foam member, and with said first suture retaining panel folded on to the needle retaining panel to form a needle retaining cavity therebetween and with said second suture retaining panel folded on to the first suture retaining panel to form a suture retaining cavity therebetween and with said fourth locking panel folded on to said needle retaining panel to lock therewith.

5. A folded retainer according to claim 1 wherein the foam member covering substantially the entire surface of one side of said first and third suture retaining panels is an integral member.

6. A folded retainer according to claim 4 wherein the fourth locking panel includes a finger and where the needle retaining panel is shorter than the first suture retaining panel and on folding the finger can be inserted between the needle retaining panel and the first suture retaining panel to interlock all panels of the retainer together.

7. A folded retainer according to claim 4 or 5 wherein there is an opening along the line connecting the first and third suture retaining panels through which the sutures pass from the suture retaining area to the needle retaining area of the retainer.

8. A folded retainer according to claim 4 wherein the needle retaining panel contains a diecut area which can be readily torn to provide access to the needled sutures.

9. A folded retainer according to claim 4 including gussets formed by dual fold lines extending over a substantial portion of the length of the fold lines between the needle retaining panel and the second suture retaining panel and between the second suture retaining panel and the fourth locking panel.

10. A folded retainer according to claims 4, 6 or 9 enclosed in an outer envelope sealed around the periphery thereof to form a suture package.

11. A suture package of claim 10 wherein a portion of the needle retaining panel extends beyond the fold line between the needle retaining panel and the first suture retaining panel and is secured in the seal around the periphery of said outer envelope.

12. A folded retainer according to claim 11 wherein said retainer includes a diecut portion extending from the portion secured in the seal around the periphery of the outer envelope to control the tearing of the needle retaining panel when the envelope is opened to provide ready access to the needled surgical sutures.

* * * * *